US00PP10688P

United States Patent [19]

Lee

[11] Patent Number: Plant 10,688

[45] Date of Patent: Nov. 17, 1998

[54] AZALEA PLANT NAMED 'CONLEJ'

[75] Inventor: Robert Edward Lee, 52063 Ridge Crest Rd., Independence, La. 70443

[73] Assignees: Robert Edward Lee; Plant Development Services Inc., both of Loxley, Ala.

[21] Appl. No.: 917,839

[22] Filed: Aug. 27, 1997

[51] Int. Cl.[6] ..... A01H 5/00

[52] U.S. Cl. ..... Plt./55

[58] Field of Search ..... Plt./55, 56, 57

*Primary Examiner*—Howard J. Locker
*Assistant Examiner*—Kent L. Bell

[57] ABSTRACT

A new and distinct variety of azalea found as a seedling in a planned cross between the female azalea 'White Jade' and the male *Rhododendron oldhamii* 'Fourth of July'. The new variety possesses a unique blooming time and is superior in development of a dense, globose shaped plant with attractive single lavender flowers.

2 Drawing Sheets

BACKGROUND OF THE INVENTION

The present invention relates to a new and distinct variety of evergreen azalea of the genus Rhododendron and a member of the Ericaceae family. This new azalea variety, hereinafter referred to as 'Conlej', was discovered by Robert Edward Lee of Transcend Nursery in August, 1986 in Independence, La. 'Conlej' originated from a planned cross hybridization between two selected breeding lines in a controlled breeding program in Independence, La. The value of this new cultivar lies in its unique blooming period, bloom color, bloom form, and growth habit.

Asexual propagation of the new plant by cuttings has been under Mr. Lee's direction at the same location. Several generations of the new plant have been evaluated and the distinctive characteristics of the plant have remained stable. The plant cannot be reproduced true from seed.

SUMMARY OF THE INVENTION

The following are the most outstanding and distinguishing characteristics of this new cultivar when grown under normal horticultural practices in Independence, La.

1. The unique spring, summer, and fall blooming.
2. A lavender flower color Red-Purple Group 73A with dotting color Red-Purple Group 64B.
3. The single flowers range in size from 2"–2½" in diameter.
4. Easily propagated with semi-hardwood cuttings in late spring through the summer.
5. Fast growth rate under normal fertilization and moisture conditions.
6. Dense and globose in nature.
7. Good specimen plant.
8. Desirable in planters.
9. Makes a very good hedge or screen.
10. Very good foundation plant for large buildings.
11. Does well as an understory plant in a woodland garden.
12. Hardy to Zone 8.
13. Attracts butterflies.

DESCRIPTION OF THE DRAWINGS

This new azalea hybrid variety is illustrated by the accompanying photographic prints in which.

1.

Figure 1:
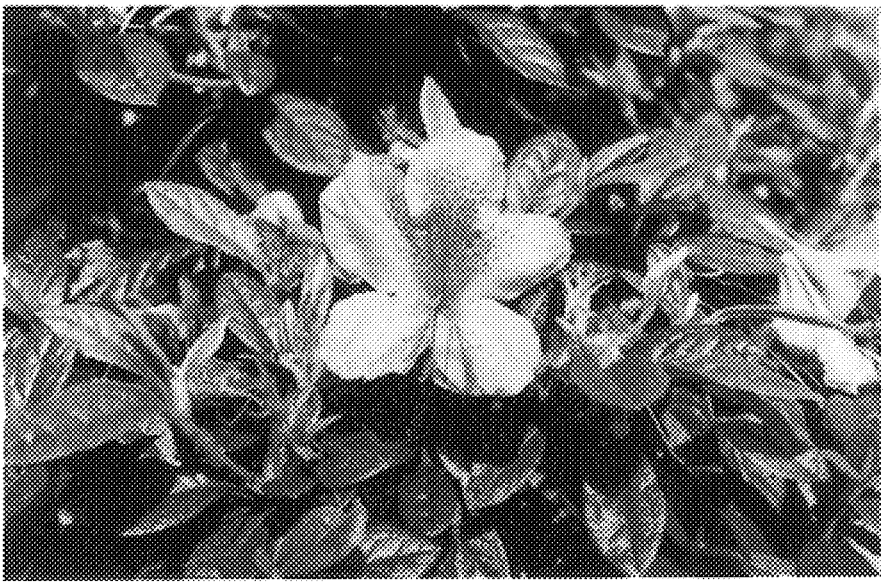
FIG. 1 is a close-up showing flower, foliage, and stem color as well as flower form.
2.
Figure 2:
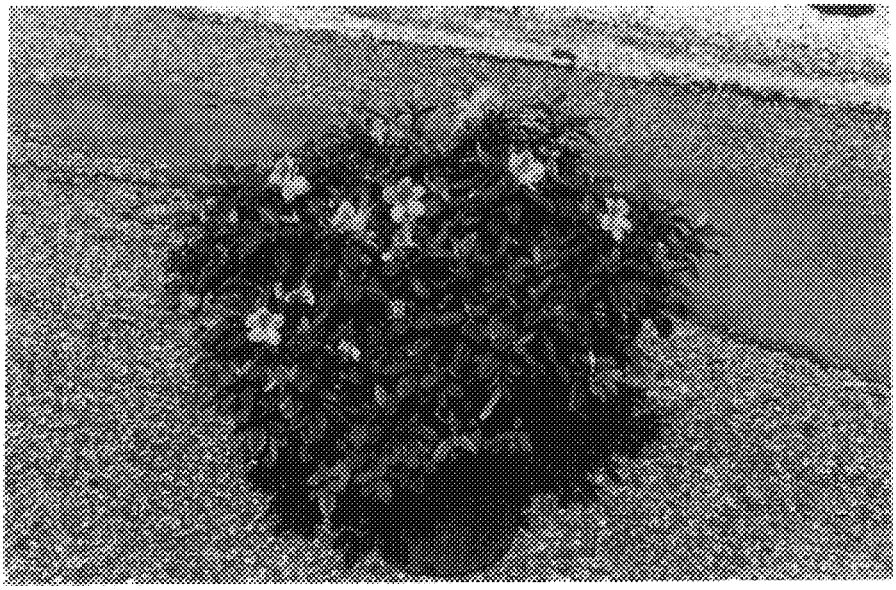
FIG. 2 shows the dense and globose growth habit of a young three gallon plant.
3.
Figure 3:
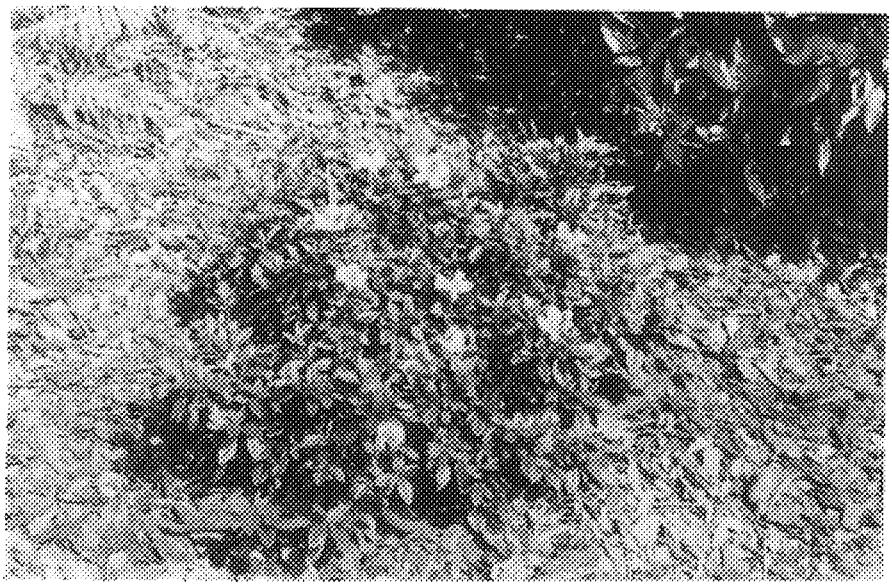
FIG. 3 shows a young plant in mid July just as it begins to bloom.
4.
Figure 4:
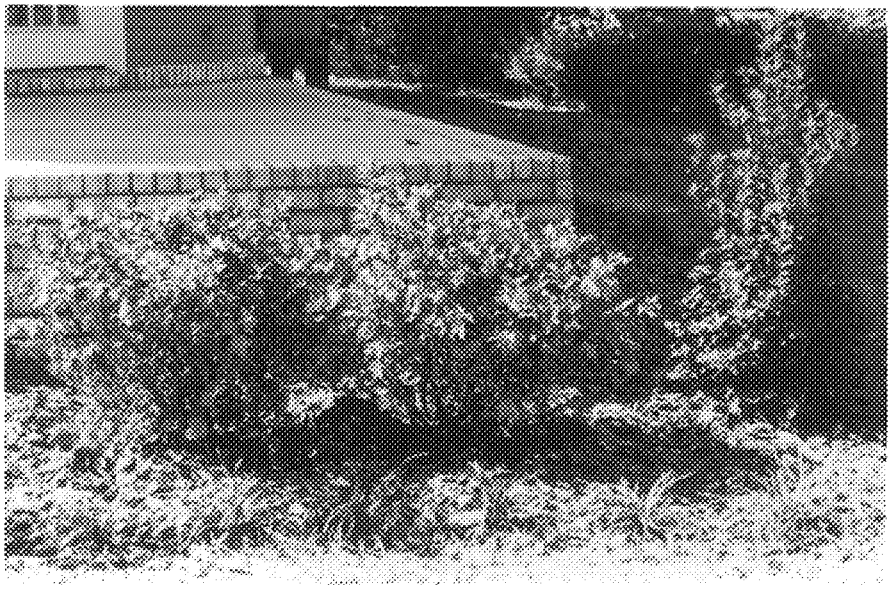
FIG. 4 shows the effective use and nature of use of the new variety in an established landscape planting.

The colors shown are as true as is reasonably possible to obtain by conventional photographic procedures. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Azalea based on my observations made of plants grown in wholesale commercial production practices, in greenhouses, and in established landscape plantings in Independence, La.

Distinctive Characteristics:

| Characteristic | 'Conlej' | 'White Jade' | *R. oldhamii* 'Fourth of July' | *R. oldhamii* |
|---|---|---|---|---|
| Height (Mature) | 5–6' | 3–4' | 8–10' | 8–10' |
| Width (Mature) | 5–6' | 4–5' | 6–7' | 6–7' |
| Flower Size | 2–2½" | 2½–3" | 1¾–2¼" | 1¾–2¼" |
| Flower Form | Single | Single | Single | Single |
| Flower Color | Red-Purple G. 73A | White G. 155D | Red G. 39A | Red G. 39A |
| Flowers per Terminal | 2–3 | 2–3 | 2–4 | 2–4 |
| Bloom Period | April | | | Mid-May > Mid-June |
| Bloom Period | Mid July > Frost | April | Mid-June > Frost | Sporadic > summer |
| Petal Number | 5 | 5 | 5 | 5 |
| Hardy Zone | 8 | 7 | 7 | 8 |
| Stamen Number | 8–10 | 10 | 7–10 | 7–10 |

The female, or seed parent, of 'Conlej' is the azalea 'White Jade'; a white, single, mid-season blooming, medium height grower. 'White Jade' is an unpatented Back Acres Hybrid developed by B. Y. Morrison in Pass Christian, Miss. Mr. Morrison first introduced these hybrids in 1964. His work was based on interest in late-blooming and double flowering clones. 'White Jade' is the result of a cross between the Glenn Dale azalea 'Helen Gunning' and the Satsuki hybrid 'Rei Ro'.

The male, or pollen, parent is *Rhododendron oldhamii* 'Fourth of July' which originated from a *R. oldhamii* seed lot collected in 1968 by Dr. Hsu of Taiwan University. The seeds were collected at 850 meters elevation on Mount Tai Tun in Taiwan. Soon after this John Patrick of Oakland, Calif. was visiting Taiwan collecting plant material of the Taiwanese Rhododendrons. He obtained a number of seedlings from Dr. Hsu and grew them in Oakland, Calif. In 1973, Dr. John T. Thornton of C&T Nursery in Franklinton, La. obtained one of the Rhododendron seedlings from Mr. Patrick. Dr. Thornton noticed in the next few years that this particular *R. oldhamii* plant was a perpetual bloomer from late June until frost on new growth. This plant produces two flushes of growth containing flowers. The second flush of growth overlaps the first flush producing a plant which blooms continuously. This differs from the species *R. oldhamii* which blooms from mid-May until mid-June and sporadically through the summer. Dr. Thornton subsequently named this plant *R. oldhamii* 'Fourth of July' in 1972.

The azalea 'Fourth of July' seems to be hardy to about 10 degrees F. (zone 7). Temperatures below this cause dieback, but the plant readily recovers and blooms profusely the following summer. *R. oldhamii* is less hardy at zone 8.

Robert Edward Lee's hybridization program was conducted with emphasis on species that are not commonly found in the genetic make-up of the present day hybrids. The 'Fourth of July' cultivar which Mr. Lee obtained from Dr. Thornton in 1981 is a heavy summer and fall blooming plant, not like the Rhododendron Species Foundation form. The flower buds form on new growth and start blooming about July 1. Mr. Lee used this species to cross with existing hybrids which have a tendency to bloom in the fall and which are also fairly hardy. As expected the resulting seedlings are heavy summer and fall bloomers with very impressive spring blooms also.

Classification:

*Botanic.*—Rhododendron hybrid 'Conlej'.

Form: Dense and rounded.

Texture: Medium.

Height: 5–6".

Width: 5–6".

Growth habit: Dense and globose. Fast growth rate under normal fertilization and moisture conditions.

Growth rate: In a period of six years from a rooted cutting the plant reaches a height of 4 feet and a spread of 4 feet. The growth rate is normally about 8 to 10" per year; the plant reaches a height of 5 to 6' at maturity while maintaining a dense habit due to the abundant branch development.

Foliage: Alternate, simple, evergreen, pubescent, elliptic, and varying in size from 1¾" to 2⅜" long and ⅝" to 1" wide. The margins are entire, with a petiole ¼" to ⅝" long. Midveins and laterals are impressed on the upper leaf surface and prominent on the underside. The base of the leaf is cuneate to attenuate and the apex is acute to mucronate. The upper surface of the immature leaves are dull, pubescent, and are Yellow-Green Group 144A and the underside is Yellow-Green Group 146D, pubescent, and matte. The upper surface of the mature leaves are Yellow-Green Group 147A, dull and slightly pubescent and the underside is Yellow-Green Group 146B, matte, and pubescent. New growth is pubescent. These hairs are initially soft and white and cover both sides of the leaf with a higher concentration on the petioles and veins. They are slightly curled, flat, and range in length from 1/32" to 1/16". As the growth matures much of the leaf pubescence is lost; however, the stems, petioles, and leaf veins retain this pubescence which becomes more setaceous and darker in color (Greyed-Orange Group 167D) through the growing season.

In 1994, the date of initial spring growth was March 10, in Independence, La. After the initial spring flush there was almost continuous growth until that fall ending October 23, also in Independence, La. When grown in full sun, the internode length of this plant is ¼" to ½"; when grown in light shade the internode length is ⅜" to ¾". As would be expected a plant grown in shade results in a taller, less dense plant with larger leaves.

The average length of terminal growth of the initial spring flush is about 5" for a plant in full sun and about 7" when grown in shade. This growth should not be trimmed since it will produce flowers starting in mid July. As the plant continues to grow through the summer and fall more flower buds are produced, which mature and bloom until frost. This remaining growth produces about 4" to 5" of height. As cool weather approaches, some of the flower buds become dormant. These buds bloom in April of the next year.

Stems: The young stems are Yellow-Green Group 146C and densely clothed with spreading white glandular hairs. During the second growing season they become Greyed-Green Group 197B, glabrous and rugose. The immature petioles, midribs, and veins are also Yellow-Green Group 146C. The pith is solid and uniform. Young and older stems are densely branched.

Buds: Tight buds at ½" are ovate and acuminate Yellow-Green Group 146D with a hairy pubescence Greyed-Orange Group 167C. The buds are borne in clusters of 2 to 3, and are sheathed by a pair of modified leaf bracts which are from ¼" to ½" long, persistent, and Yellow-Green Group 147A. The pedicel is ⅝" to ¾" long, pubescent, and Red Group 53B. The calyx is ⅜" to ½" long, Yellow-Green Group 144B, funnel shaped, persistent, and pubescent. The five imbricated sepals are narrowly lanceolate and joined at the base to form a cup. As the buds swell the bud sheath matures to a Greyed-Orange Group 165A, falls off, and reveals the flower color Red-Purple Group 73A.

Flowers: Perfect, single, Red-Purple Group 73A (front and back), glabrous, openly funnel shaped, 2" to 2½" wide by 1¾" to 2¼" long, borne on current season's growth, non-fragrant; they last on the plant in the garden 5 to 6 days. There are 5 true petals which are fused at the base and elliptic to obovate. The dorsal lobe and the two upper wings of these true petals are dotted Red-Purple Group 64B. There are from 8 to 10 non-petaloid stamen. The stamen are 1½" to 1⅞" long and the filaments are Red-Purple Group 73A. The anthers are also Red-Purple Group 73A and the pollen is Yellow Group 11D. The pistil is single, non-petaloid, 1½" to 2" long, and Red Group 54A. The ovary is densely glandular-setose and has five locules. The capsule matures in about 5 months, in Independence, La., to about ¼" to ½" long; it has a persistent style, is Yellow-Green Group 146A, and contains from 100 to 300 nonwinged seeds. Normally fruit set is not heavy. There is a 2 to 3 week flowering period in April in Independence, La. Flowering resumes in mid July as the new buds mature and continues until frost which can be as late as November or December in Independence, La. Azaleas blooming at this time of year attract butterflies in profusion.

Culture: Grows well in a wide range of conditions, tolerates sun to shade. Prefers a moist, well-drained soil that is rich in organic matter. Responds well to mulching and medium applications of fertilizer; prefers ph 5.0 to 5.5. Very little pruning is needed; adaptable to container and above ground planters; makes a good foundation plant or informal hedge with excellent foliage and flower contrast. Ideal for coastal regions and warmer parts of Piedmont. Propagated with semi-hardwood cuttings in late spring through the summer.

Pests: Lace wing and spider mites can be a problem.

I claim:

1. A new and unique variety of azalea plant named 'Conlej' as herein shown and described.

* * * * *